United States Patent [19]

Kasting, Jr. et al.

[11] Patent Number: 5,520,893
[45] Date of Patent: May 28, 1996

[54] APPARATUS WITH SAFETY MEANS FOR STERILIZING ARTICLES WITH OZONE

[75] Inventors: John R. Kasting, Jr., Waxhaw; Ronald G. Potter, Monroe, both of N.C.

[73] Assignee: OxiDyn, Incorporated, Monroe, N.C.

[21] Appl. No.: 129,760

[22] Filed: Sep. 29, 1993

[51] Int. Cl.$^6$ ........................................................ A61L 9/00
[52] U.S. Cl. .......................... 422/305; 422/117; 422/292; 422/301
[58] Field of Search ........................ 422/186.07, 186.12, 422/186.14, 186.15, 186.2, 22, 23, 28, 30, 31, 292, 296, 301, 305, 907, 117, 118, 106, 107, 110; 220/DIG. 20, 230; 250/455.11

[56] References Cited

U.S. PATENT DOCUMENTS

| | | | |
|---|---|---|---|
| 3,549,528 | 12/1970 | Armstrong | 422/186.14 X |
| 3,604,895 | 9/1971 | MacKay | 422/118 X |
| 3,719,017 | 3/1973 | Shapiro et al. | 422/186.07 X |
| 3,876,385 | 4/1975 | Markus et al. | 422/118 |
| 4,122,969 | 10/1978 | Hugley | 220/DIG. 20 X |
| 4,141,956 | 2/1979 | Lemchen et al. | 422/301 X |
| 4,410,492 | 10/1983 | Kaye | 422/27 |
| 4,430,306 | 2/1984 | Namba et al. | 422/292 |
| 4,447,399 | 5/1984 | Runnells et al. | 422/113 |
| 4,517,159 | 5/1985 | Karlson | 422/31 X |
| 4,619,763 | 10/1986 | O'Brien | 210/177 |
| 4,627,924 | 12/1986 | Coste | 422/186.12 X |
| 4,637,916 | 1/1987 | Hennebert et al. | 422/36 |
| 4,863,701 | 9/1989 | McMurray | 422/1816.14 X |
| 4,954,321 | 9/1990 | Jensen | 422/186.14 X |
| 4,988,484 | 1/1991 | Karlson | 422/186.2 X |
| 5,057,283 | 10/1991 | Guggenheim et al. | 422/116 |
| 5,069,880 | 12/1991 | Karlson | 422/186.19 |
| 5,082,558 | 1/1992 | Burris | 422/301 X |
| 5,207,993 | 5/1993 | Burris | 422/256 |
| 5,256,377 | 10/1993 | Nakamaru et al. | 422/122 |
| 5,266,275 | 11/1993 | Faddis | 422/116 |

*Primary Examiner*—Robert J. Warden
*Assistant Examiner*—Krisanne M. Thornton
*Attorney, Agent, or Firm*—Bell, Seltzer, Park & Gibson

[57] ABSTRACT

Medical instruments, including stainless steel, plastic tubing, and the like, are sterilized in a portable apparatus that provides a low volume, high pressure flow of continuously circulating water containing about 2 to 6 ppm of ozone. The portable apparatus includes a housing having an open chamber for containing medical instruments. Within the housing are a high voltage transformer, an ozone generator, and a high pressure, low volume pump for circulating ozonated water. A lid for the chamber is provided with carbon substantially to preclude ozone from escaping from the chamber into the atmosphere outside the housing. The lid includes a safety switch so that the apparatus will not operate unless the lid is in place.

21 Claims, 5 Drawing Sheets

5,520,893

APPARATUS WITH SAFETY MEANS FOR STERILIZING ARTICLES WITH OZONE

FIELD OF THE INVENTION

This invention relates to methods and apparatus for sterilizing articles. More specifically, this invention relates to methods and apparatus that use ozone as the sterilant.

BACKGROUND OF THE INVENTION

Ozone can be used in the purification of drinking water, in industrial waste water treatment, for deodorizing air and sewage gases, as a bleach for waxes, oils, wet paper, and textiles, as an oxidizing agent in chemical processes, and is an effective bactericide and virucide. Numerous apparatus and methods have been proposed for using ozone as a purifying agent, a sanitizing agent, a disinfectant, and as a sterilant. Typically, the ozone is generated in an ozone generator and then contacts the article to be treated either as a gas or dissolved in water.

For example, Burris U.S. Pat. No. 5,082,558 describes several systems for using ozone in small quantities to purify contact lenses in from about 2 to 10 minutes. In one embodiment, air is pumped into an ozone generator to generate ozone and the air and ozone mixture is bubbled into water in a chamber for direct contact with contact lenses. In another embodiment, a mixture of ozone, air, and water enters a gas and liquid separator where undissolved ozone is removed and water with some dissolved ozone is sent to a chamber for contact with the contact lenses. In another embodiment, the ozone and water may be mixed in a pump and in a static mixer and the mixture of ozone and water enters the contact lens treatment chamber. An ozone reducer is provided to destroy undissolved ozone that is vented through a porous hydrophobic resin, either through the cover of the lens chamber or the gas and liquid separator, but the quantities of ozone used are so small that no health hazard is said to be presented if raw ozone escapes into the atmosphere. Additional embodiments show spraying of contact lenses with a spray of water and ozone.

Karlson U.S. Pat. No. 5,069,880 describes the use of a high pressure ozone generation system for water treatment and for sterilization. The ozone is bubbled into water in a tank to produce a wet gas for use in a separate sterilizing chamber. Forced circulation of the gas distributes the gas through the load for sterilization.

However, surgical and dental instruments typically are sterilized by application of steam in an autoclave and are then wrapped in a sterile wrap until needed. Use of a steam autoclave for sterilization is somewhat time consuming. Physicians, veterinarians, and dentists typically are required to purchase several sets of instruments and to keep several sets on hand in a sterile condition available for immediate use.

Ozone sterilization typically is still not used to sterilize medical and dental instruments despite ozone's many benefits as a sterilant. Ozone generation and use can be problematic for the quantities required for sterilization. For example, ozone should be generated on site and should be used as it is generated because ozone breaks down too quickly for later use at another location. It is undesirable to allow ozone gas to be released into the confined atmosphere of a home or office, and larger quantities can be considered a health hazard. Electrically generating the relatively large quantities of ozone required for sterilization, as opposed to, for example, purification, requires that a relatively high voltage be developed in the sterilization apparatus. High voltage can pose a risk to the user of the apparatus.

SUMMARY OF THE INVENTION

The present invention provides an easily and safely operated apparatus having a minimum of components for sterilizing articles such as medical instruments. The articles can be placed in a chamber through which a water supply containing ozone sufficient for sterilization is distributed and circulated. A lid is provided for closing the chamber that contains an ozone destroying substance to prevent ozone from escaping from the chamber. The apparatus is rendered inoperable if the lid is opened.

Specifically, the invention provides a portable and self-contained apparatus for sterilizing articles that includes an open chamber associated with a housing for containing the articles to be sterilized. The chamber is positioned for receiving the articles to be sterilized and for receiving a recirculated supply of water and ozone at low volume and high pressure for immersion contact with the articles to be sterilized. A lid is associated with the open chamber so that the chamber can be closed and the ozone substantially can be precluded from escaping from the chamber when the apparatus is being operated. Also included are a means for recirculating flow of the ozone and water through the chamber including a high voltage transformer and ozone generator located within the housing for generating the ozone and a means for injecting the ozone generated by the generator into the water for recirculation.

In a more specific embodiment, the lid for the chamber contains a carbon filter that destroys ozone upon contact. The lid includes a magnetic safety switch to prevent operation of the apparatus when the lid is opened.

The present invention also includes a method for disinfecting articles wherein articles are placed in a chamber for sterilization, the chamber is closed, and a water supply containing ozone continuously is circulated through the chamber to sterilize the articles. Ozone escaping from the water in the chamber is destroyed before it can escape from the chamber and the method is inoperative unless the step of destroying ozone is performed.

More specifically, the water containing ozone is recirculated through the chamber at a pressure from at least about 25 to 40 psig and at a rate of from at least one to four gallons per minute. Ozone is present in the water in a range of from about 0.2 ppm to 0.6 ppm, preferably 0.4 ppm.

Thus the benefits of the invention are realized in an apparatus and method for sterilizing articles by contact with a circulating water supply that contains ozone sufficient for sterilization in which ozone escaping from the water is destroyed before entering the atmosphere surrounding the apparatus, and in which the apparatus is rendered inoperable unless the ozone is destroyed. The apparatus is useful for medical instruments and is suitable for use in physicians', veterinarians', and dentists' offices.

BRIEF DESCRIPTION OF THE DRAWINGS

For a more complete understanding of this invention, reference should now be had to the embodiment illustrated in greater detail in the accompanying drawings and described below in an example of the invention. In the drawings.

DETAILED DESCRIPTION OF THE INVENTION

Figure 1:
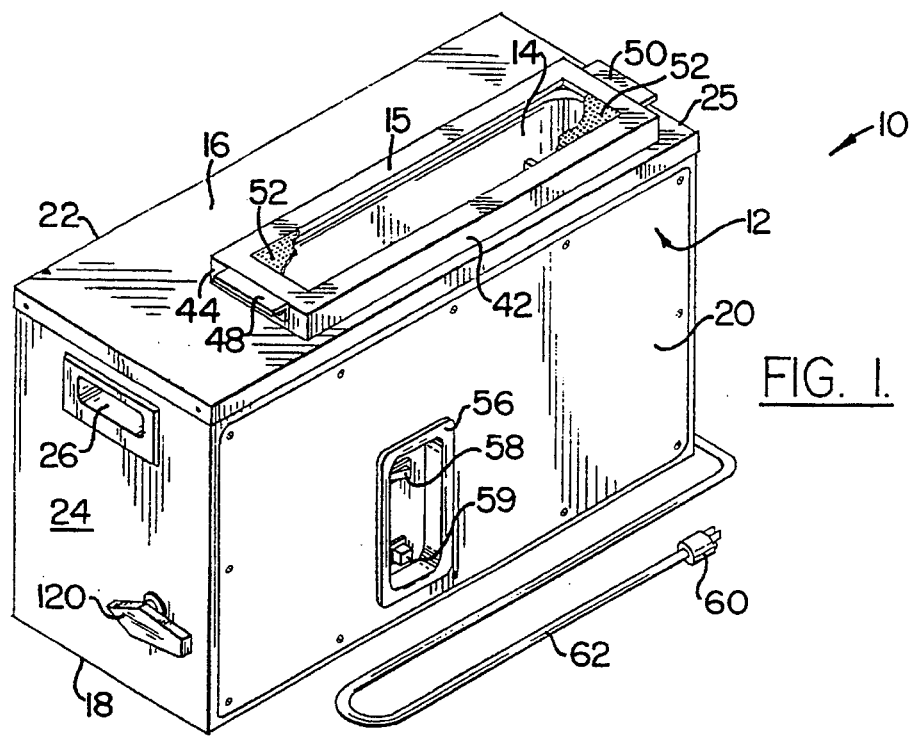
FIG. 1 represents a perspective view taken from the front, top, and left side of an apparatus of the invention and showing the lid partially cut away.

FIG. 1 shows generally at 10 a portable sterilizing unit for sterilizing medical instruments, and, in particular, veterinary medical instruments for surgical use. Such instruments include stainless steel clamps and scalpels and plastic tubing for fluids, including gases and liquids. The sterilizing unit uses a recirculating supply of ozone dissolved in water as the sterilant, as is explained below. Ozone or $O_3$ is an allotropic form of oxygen that exists as an unstable blue gas with a pungent odor. Ozone readily is produced from air or other oxygen containing gas by passage of a high voltage electrical discharge through a stream of the oxygen containing gas.

Ozone is a more active oxidizing agent than oxygen and is more soluble in water. Ozone destroys bacteria, viruses, and other micro-organisms on contact. Unlike many other disinfecting agents, ozone is used as it is generated, breaks down rapidly, and does not leave chemical residues. For sterilization of medical instruments, which is the condition of being free from bacteria and other microorganisms, the ozone should be present in water in an amount of from at least about 0.2 ppm to 0.6 ppm. Typical operation of the sterilizing unit described below should produce about 0.4 ppm.

Continuing with FIG. 1, a housing 12 fabricated from stainless steel sheet metal houses the ozone generating and recirculating equipment and includes a chamber or instrument sterilizing pan 14 (FIG. 2) through which water and dissolved ozone are circulated and in which medical instruments are ozonized. Sterilizing pan 14 can be seen in FIG. 1 through the partially broken away view of a lid 15 for the instrument sterilizing pan.

The housing 12 comprises top and bottom panels 16 and 18, front and rear panels 20 and 22, and end panels 24 and 25 (FIGS. 2 and 5), all of stainless steel sheet metal. Stainless steel is relatively easy and economical to fabricate, resistant to ozone oxidation, relatively easily cleaned, and has an attractive appearance for use in medical facilities. Other mediums including plastics and other metals may be chosen for fabricating the housing, but stainless steel is preferred.

Figure 4:
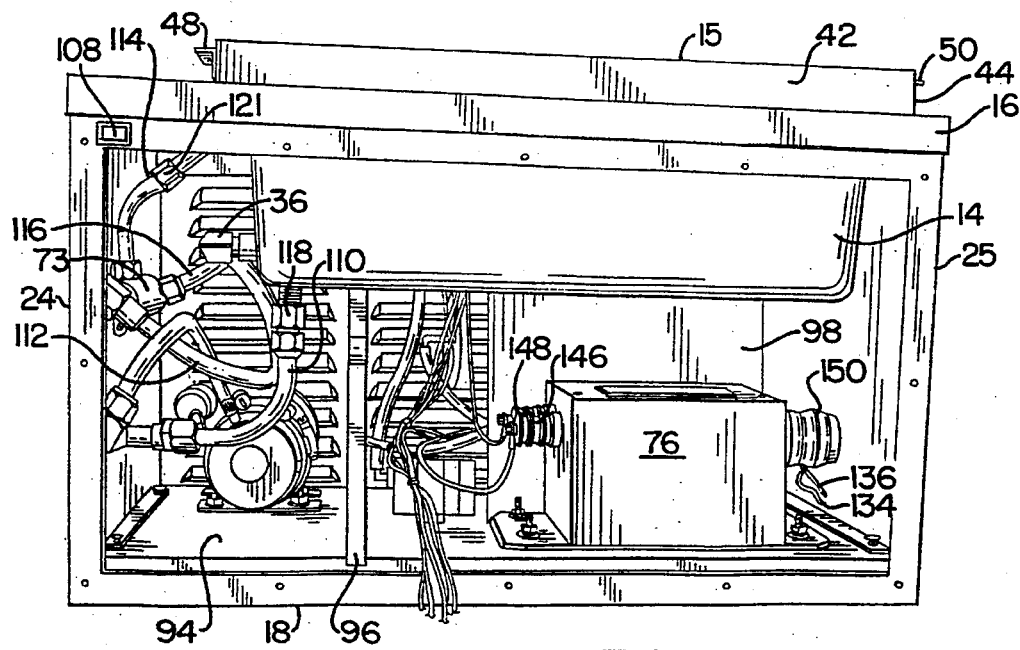
FIG. 4 shows a plan view taken from the front of the apparatus of FIG. 1 with the front panel of the housing removed and showing the internal components of the apparatus.
Figure 5:
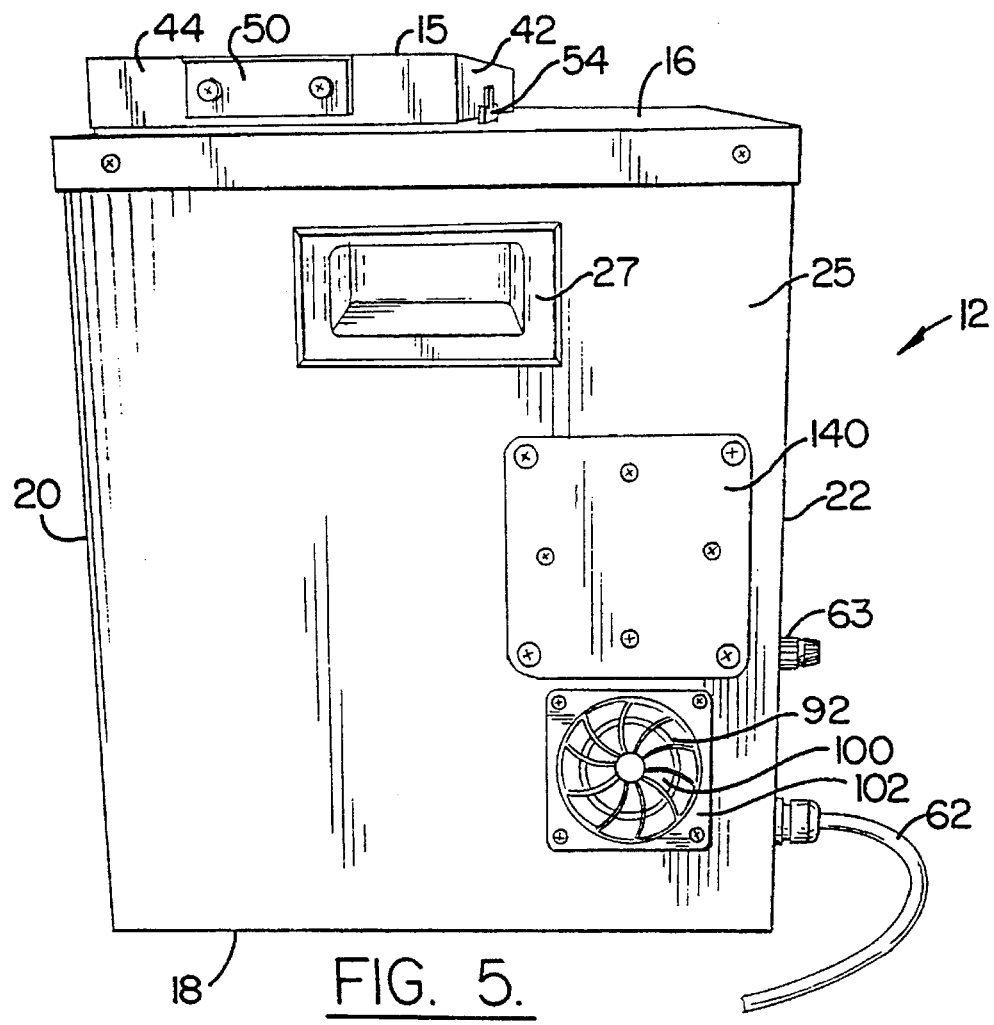
FIG. 5 shows a side elevational view of the apparatus represented in FIG. 1 taken from the right hand side.

End panels 24 and 25 include recessed handles 26 and 27, respectively (FIGS. 1 and 5). Recessed handles 26 and 27 provide a convenient means for lifting and transporting the unit. (The sterilizing unit represented in the drawings and as discussed herein weighs about seventy (70) pounds.) Top panel 16 is fabricated integrally with sterilizing pan 14 as shown (FIGS. 1, 2, and 4) from a single piece of stainless steel sheet metal. However, it should be apparent to the skilled artisan that the top panel and sterilizing pan could be fabricated as separate components so that the pan could be removable from the housing if desired.

Figure 2:
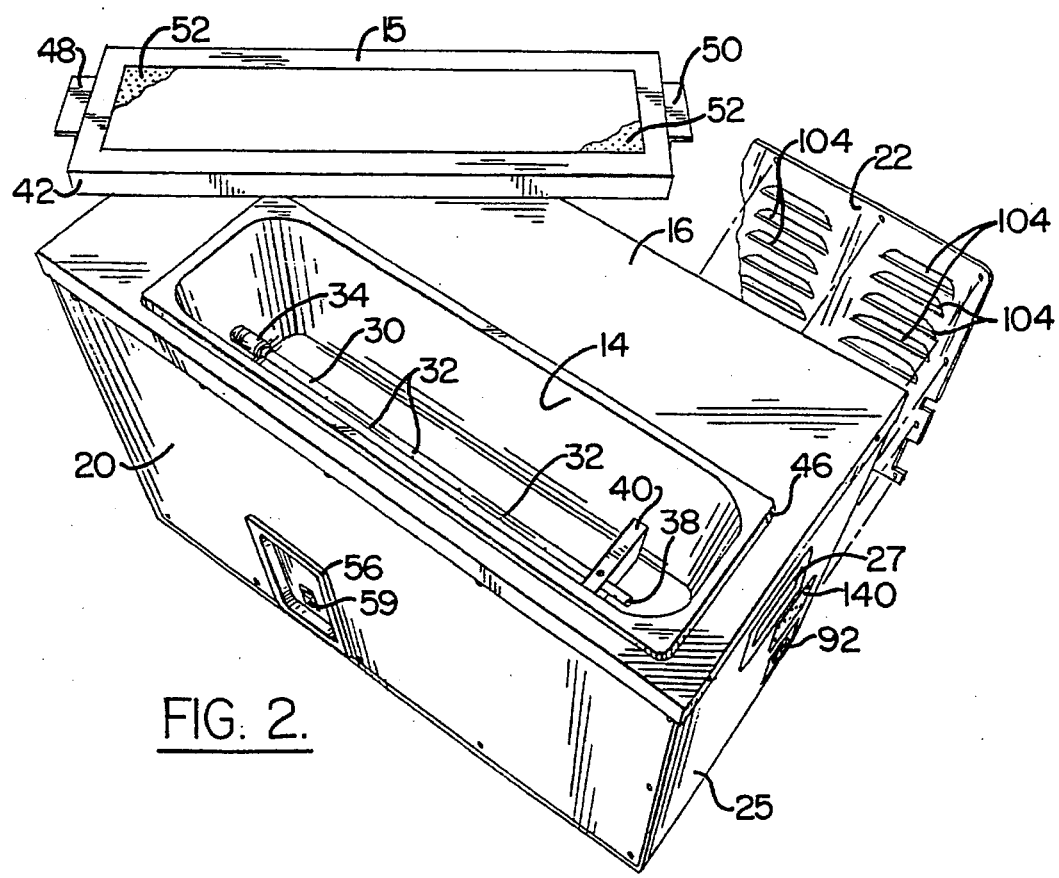
FIG. 2 shows a perspective view taken from the front, top, and right side of the apparatus of FIG. 1 and showing the lid partially cut away and removed and the rear panel of the housing in a fragmentary and exploded view.

FIG. 2 shows the internal details of the instrument sterilizing pan 14. An elongate, hollow, distributor bar 30 is provided with numerous, spaced, radially extending orifices 32 for evenly distributing water with ozone dissolved therein into the instrument sterilizing pan. The distributor bar is connected to a fitting 34 at one end thereof that extends through the pan wall and is connected to a source of water and dissolved ozone 36 (FIG. 4). The distributor bar is capped at the opposite end 38 and is supported adjacent that end by a supporting member 40. Supporting member 40 preferably is made of polyethylene or stainless steel, both of which are resistant to oxidation by ozone.

As shown in FIGS. 1 and 2, the removable lid 15 that is provided for the instrument sterilizing pan 14 substantially seals the pan and substantially precludes undesirable foreign objects from entering the pan and ozone gas from escaping from the pan into the surrounding atmosphere. Lid 15 includes raised side and end panels 42 and 44, respectively, that fit over the raised edge 46 of the instrument sterilizing pan. Handles 48 and 50 are provided on each end of the lid so that the lid easily may be removed from the pan for obtaining access to the pan and placing instruments into and removing instruments from the pan.

Alternatively, other arrangements are envisioned for opening the sterilizing pan. For example, lid 15 could be hinged to top panel 16 for opening the sterilizing pan. Lid 16 could be fitted over the raised edges 46 of the sterilizing pan so as to slide or pivot with respect to the pan to provide an opening for placing instruments into the pan. Essentially any arrangement can be used that provides for a secure fit of the lid over the open chamber and yet also provides for ease in opening the chamber.

Lid 15 further comprises a stainless steel perforated center panel 52 (partially broken away view). Center panel 52 contains an activated carbon filter medium or other suitable substance that decomposes ozone on contact and substantially precludes ozone from escaping from the sterilizing pan into the atmosphere when the lid is in place.

A magnetic safety switch 54 (FIGS. 3 and 5) is provided on the lid 15. The magnetic safety switch is a low amperage switch (about 0.1 amp) similar to a proximity switch and generates a magnetic field. As explained below in connection with FIG. 7, if the lid is removed from the unit, then the circuit is broken and the unit becomes inoperative. In the embodiment represented in the drawings, the magnetic safety switch must be in place with the lid on the housing and covering the instrument sterilizing pan for the apparatus to operate.

Turning now to front panel 20 as shown in FIG. 1, the sterilizing unit is operated from a switch plate 56 located on front panel 20. A power switch, on/off switch 58 on the switch plate, controls electrical power to the sterilizing unit and preferably is illuminated to signal the operator that power is provided. Reset switch 59, preferably an illuminated push button switch, is used by the operator to activate a timed sterilization cycle, as explained below.

Figure 3:
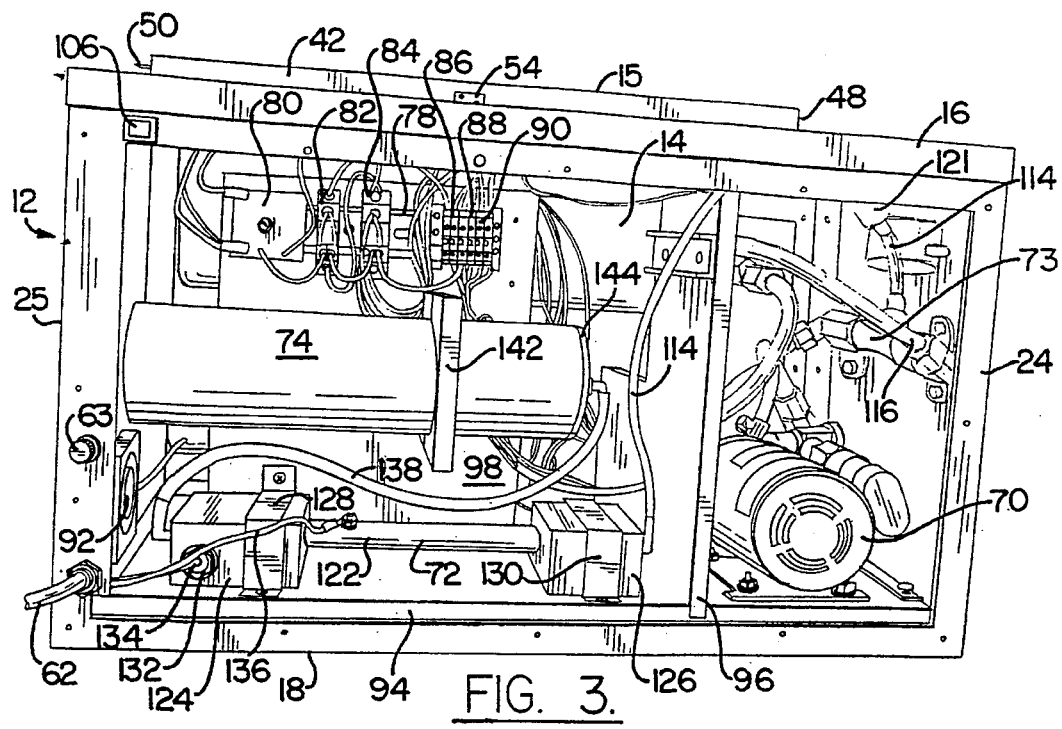
FIG. 3 shows a plan view taken from the rear of the apparatus of FIG. 1 with the rear panel of the housing removed and showing the internal components of the apparatus.

Power to the unit preferably may be provided from standard household current, such as is provided through male plug 60 and electrical connector cord 62 from a typical wall outlet source, including the 50/60 cycle, 110, 115, or 120 volts AC wall outlets that are found in various regions of the United States and some foreign countries. Electrical connector cord 62 enters housing 12 through the stamped right angle edge of end plate 25, which forms the support for rear panel 22 (FIGS. 3 and 5). Fuse 63 (FIGS. 3 and 5), which is located adjacent the entry point into the housing of electrical cord 62, provides protection from power overloads for the electrical components inside the housing.

Figure 6:
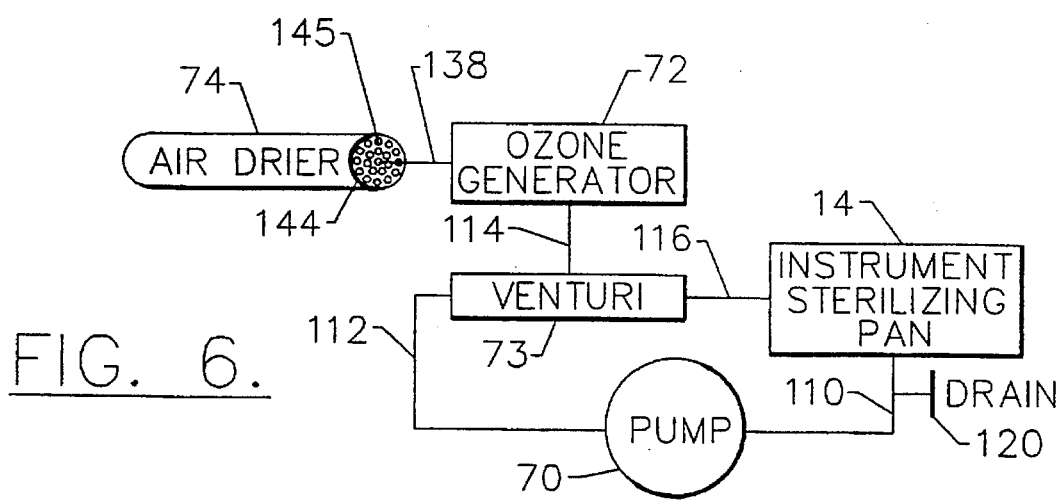
FIG. 6 represents a simplified process flow schematic diagram for the apparatus of FIG. 1.

FIG. 3 shows a plan view of the sterilization unit with the rear panel 22 removed to reveal the internal components of the sterilization unit. The simplified process flow diagram of FIG. 6 shows the flow of gas and liquid through the components of FIG. 3. A pump 70 circulates water and dissolved ozone through the sterilizing pan 14. An ozone generator 72 supplies ozone for injection through a venturi 73 into the water for circulation on the discharge side of the pump. The ozone is created from air that has been dried in an air drier 74. A high voltage transformer 76 (FIG. 4) supplies electrical power to operate the generator. Power is supplied to the pump, the transformer, and various other electrical components through a terminal strip 78 (FIG. 3) that receives electrical power from cord 62 when plugged into a suitable source and when power switch 58 and reset switch 59 are engaged. Terminal strip 78 includes a timer relay 80, a safety relay 82, a circuit relay 84, and terminal pairs 86, 88, and 90 for controlling and distributing power to a fan 92 (FIGS. 3 and 5), the pump, and the transformer, respectively. Electrical circuitry for these components is described below with particular reference to FIGS. 7A, 7B, and 7C.

Also shown in FIG. 3, polyethylene panels 94, 96, and 98 of approximately one-quarter inch thickness each provide insulation from heat and electrical discharges and assist substantially in precluding discharge of electrical current through the housing, thereby promoting safety in the operation of the unit. Terminal strip 78 is mounted to polyethylene panel 98 for distributing power. Together, panels 94, 96, and 98 divide the unit interior into three compartments: one housing the transformer, one housing the pump, and one housing the air drier and ozone generator. Most of the heat is generated by the pump, which is separated from the other components by the polyethylene panels.

Polyethylene panel 94 provides a mounting shelf for the pump 70, generator 72, transformer 76, and panels 96 and 98 that enables easy assembly, insertion, and removal as a whole of substantially the entire components of the unit. Polyethylene is preferred, which is inert to ozone, is virtually nonconductive, and is stable with respect to heat likely to be encountered in operation of the apparatus, although other suitable materials are also available, as should be apparent to the skilled artisan.

Heat generated by operation of the unit is dissipated by fan 92 (FIG. 3) which is mounted in an orifice 100 (FIG. 5) in end panel 25 of housing 12. The orifice in the end panel is covered by a cover plate 102 for the fan blades. Fan 92 also circulates fresh ambient air through the interior of the housing. This fresh air is used to make ozone, as explained below. The fan works in cooperation with louvered vents 104 in rear panel 22 (FIG. 2) to draw fresh air either through the fan or through the vents, depending on whether the fan exhausts air from the housing through orifice 100 or pulls air into the housing through orifice 100. The fan preferably operates on 120 VAC and should be rated to move about 100 cubic feet per minute of air.

As shown in FIGS. 3 and 4, the top and bottom panels 16 and 18, respectively, and end panels 24 and 25 are fabricated so that the primary access to the electrical components within the housing is through the front and rear panels 20 and 22. Normally open mechanical safety switches 106 and 108 (FIGS. 4 and 3, respectively) substantially preclude completion of the electrical circuit through power switch 58, and supply of electrical power to the sterilizing unit, unless front and rear panels 20 and 22 are in place and secured to the unit to close the switches.

Turning now to a detailed discussion of the major internal components of the sterilizing unit, pump 70 (FIGS. 3 and 6) is a nutating pump that is capable of providing a low volume, high pressure flow of water at a steady rate. Pump 70 preferably is self priming so that the operator primes the pump by filling the sterilizing pan 14 with the desired level of water. The suction side of the pump is flooded by gravity flow of water through sterilization pan discharge conduit 110. The pump circulates water and dissolved ozone through the sterilization pan at a pressure of from at least about 25 to 40 psig and a volumetric flow rate of from at least about one to four gallons per minute. Preferred operation with an appropriately sized venturi is at 30 psig and 1½ gallons per minute. Pumps meeting these specifications are commercially available from a variety of sources.

Typically, complete sterilization can be obtained in about fifteen minutes when the ozone concentration is about 0.4 ppm of water, the flow rate is 1½ gallons per minute, and the pressure is 30 psig. Small particles of flesh typically also are removed during the sterilization cycle, although preferable practice is to remove the particles by washing the instruments prior to sterilization.

The pump discharge passes through conduit 112 to venturi 73 (FIGS. 3 and 6). The fluid flow path through the venturi gradually narrows to create a flow path of reduced cross sectional area. This reduced flow path causes the fluid to flow at an increased rate and creates a negative pressure condition or vacuum that pulls ozone into the venturi for injection into the fluid from ozone generator 72 through conduit 114. As will be apparent to the skilled artisan, the venturi should be sized based on the flow rate and pressure generated by the pump. Ozone gas is injected into the water for circulation at the venturi and passes through conduit 116 through fitting 36 into distribution bar 30 for distribution into the sterilizing pan as described above with reference to FIG. 1. The sterilizing pan includes an aperture in the bottom of the pan adjacent fitting 34 and connected to fitting 118 on discharge conduit 110 of the sterilization pan for gravity discharge of the water from the pan and return to the intake side of the pump through conduit 110. Alternatively, the water can be discharged from the unit through conduit 110 by opening the drain cock 120 on end panel 24 (FIG. 1).

Ozone generator 72 supplies ozone for injection into the water through conduit 114 to the venturi. A check valve 121 or other back flow preventing device should be positioned between the ozone generator and the venturi substantially to preclude water from entering the ozone generator.

Ozone generator 72 (FIG. 1) is a corona discharge generator that does not introduce potentially harmful substances into the water for circulation and sterilization. In the illustrated embodiment, a single mercury-free corona lamp, which is a glass tube containing a mixture of argon and neon gasses, and which contains a central wire electrode, is surrounded by a stainless steel jacket electrode 122. More than one such combination of corona tube and jacket electrode can be used to increase ozone output, if desired.

An air gap separates the corona lamp and the jacket electrode 122. The corona tube is retained in place in the jacket electrode, centered and spaced from the jacket electrode, by silicone retainer rings having radially directed spaces for the passage of air through the gap between the glass tube and the jacket electrode. A corona lamp of the type used in the ozone generator of the invention is available from LCD Lighting, Inc., Milford, Conn. Silicone retainer rings of the type described are available from Seal Jet, Inc., Charlotte, N.C.

The ends of the corona tube and stainless steel jacket electrode are mounted in substantially nonconductive blocks 124 and 126, which are formed of polyvinylchloride and are secured to polyethylene panels 94 and 98 through mounting strips 128 and 130, respectively, substantially as shown. An additional corona tube and jacket electrode can be mounted in blocks 124 and 126 and powered by the same transformer if desired to increase ozone output.

Block 124 includes an orifice 132 for receiving a lead wire 134 from the output electrodes of transformer 76. Inside block 124, the lead wire 134 electrically is connected to the central wire electrode of the corona tube. A lead wire 136 from the output electrodes of the transformer electrically is also connected to the stainless steel jacket. High voltage supplied from the transformer to the ozone generator electrodes causes ozone to form from the oxygen in the air in the space between the outer electrode and the corona lamp.

Air is supplied through conduit a fluid flow conduit 138 to the space between the corona tube and the outer electrode through block 124 and air enriched in ozone is withdrawn through the opposite block 126. The negative pressure created by water flowing through venturi 73 pulls air through conduit 138, the ozone generator, and conduit 114 so that a stream of fresh air continuously is available for the creation of ozone in the ozone generator when the water pump is operating.

Dry air is preferred for the production of ozone because moisture in the air interferes with the production of ozone. Accordingly, air drier cartridge 74 (FIG. 1) having a silica and alumina desiccant is provided for ensuring that a supply of dry air is available for the production of ozone. This desiccant is not self re-generating, but can be fabricated with a low resistance to air travel. Low resistance to the flow of air through the desiccant enables the apparatus of the present invention to be constructed without the use of a compressor and greatly reduces the weight and increases the portability of the apparatus. The negative pressure created by water flowing through venturi 73 is sufficient to pull air through air drier cartridge 74 and into ozone generator 72 through fluid flow conduit 138. An air drier cartridge suitable for use in the practice of the present invention is available from Dominic Hunter, Inc. having worldwide offices and an office at Charlotte, N.C.

Air drier cartridge 74 is fixed at one end thereof to a plate 140 (FIG. 5) that covers an orifice in end panel 25. The orifice is sized so that the plate can be removed from the end panel and a spent air drier cartridge can be withdrawn from the interior of the housing through the orifice and replaced with a fresh cartridge without having to remove the rear panel 22. The air drier is supported adjacent its opposite end by a polyethylene bracket 142 having a central aperture that is mounted on polyethylene panel 98. The bracket is split so that the air drier cartridges are more easily inserted and removed.

The air drier cartridge 74 is a plastic housing having an end cap 144 (FIGS. 3 and 6) with numerous apertures 145 (FIG. 6) through which air is admitted to an annular space within the housing. The annular space surrounds a centrally located passageway for dry air. The annular space is filled with a silica and alumina desiccant. Air is drawn through the apertures in the end cap through the desiccant to the opposite end of the dryer where the dried air enters the central passageway and travels the full length of the air drier in a direction opposite to the incoming air. The dry air enters conduit 138 and is pulled through conduit 138 to the ozone generator at block 124 where the dry air is enriched in ozone. The ozone enriched air is then pulled into the venturi for injection into the recirculating water.

FIG. 4 shows transformer 76 for converting line voltage and supplying high voltage to ozone generator 72 for creating ozone. Transformer 76 preferably is an inductive, step-up, high voltage transformer that can receive as line voltage standard household current so that an operator conveniently and safely can plug the unit into a suitable wall outlet. Typically the primary or input voltage to input electrodes 146 and 148 will be from 110 VAC to 120 VAC. A 120 VAC 50/60 cycle primary is preferred for most geographical locations. Secondary or output voltage from output electrodes for lead wires 134 and 136 may vary from about 8000 volts to 12,000 volts. Neoprene jackets 150 are provided for the high voltage output electrodes to reduce the risk of electrical shock to persons having access to the interior of the housing. Voltage much less than 8000 volts typically does not generate sufficient ozone for sterilization; voltage above about 12,000 volts typically produces arcing in the ozone generator and results in problems. Preferably, secondary or output voltage will be about 9000 volts. Most preferred for operating the ozone generator is a high voltage transformer having a 120 VAC 50/60 cycle primary coil and a 9000 volt secondary coil. A suitable transformer is available from Magnetics and Controls, Inc., Rosemont, N.J.

Figure 7A:
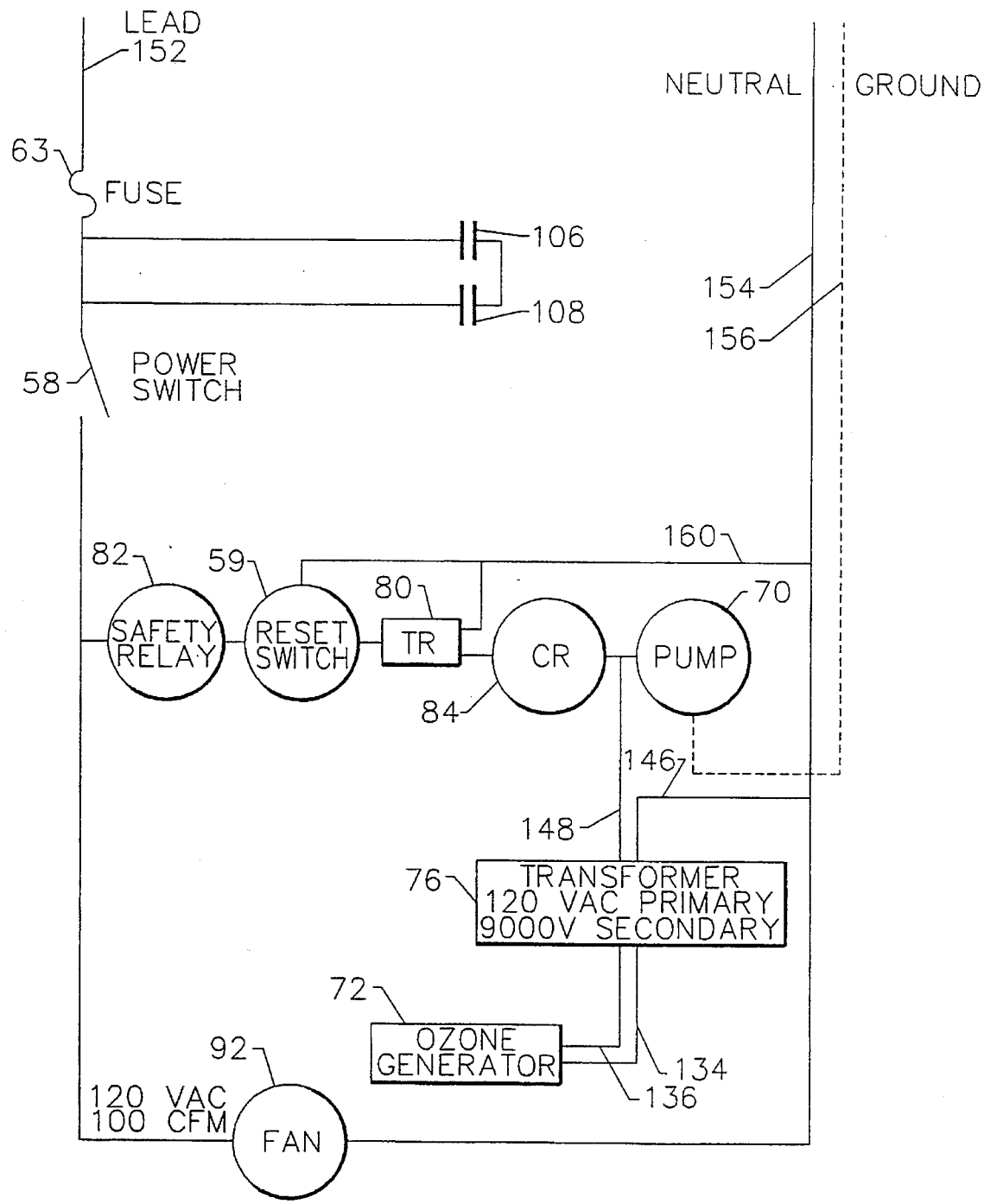
FIG. 7A represents a simplified electrical schematic diagram for the apparatus of FIG. 1.
Figure 7B:
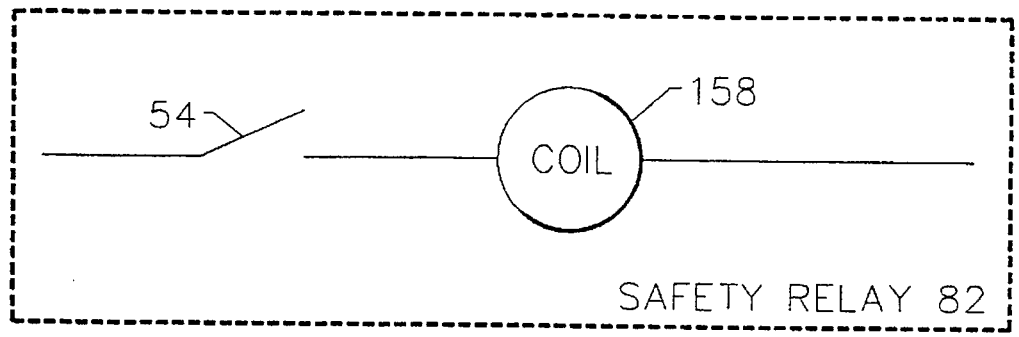
FIGS. 7B and 7C represent the elements of selected portions of the electrical schematic of FIG. 7A.
Figure 7C:
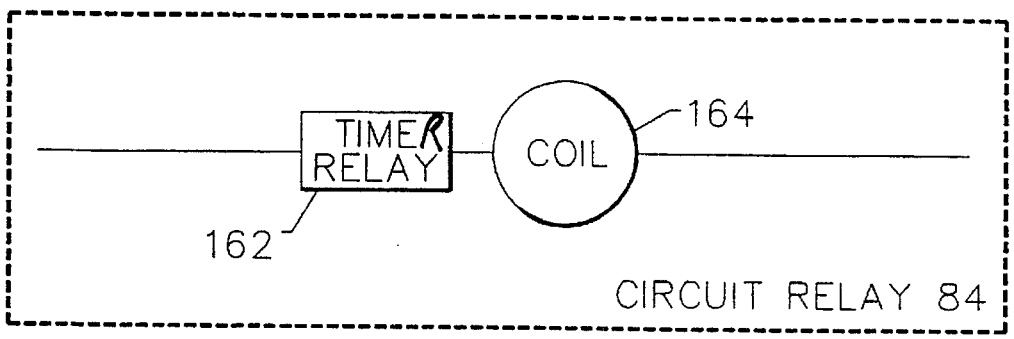

Turning now to a discussion of the electrical circuitry used for operating the unit, FIG. 7A illustrates in schematic form the wiring and electrically operated components for operation of the sterilizing unit. FIGS. 7B and 7C show selected components of FIG. 7A in more detail. Power is supplied through lead wire 152 of electrical connector cord 62 (FIG. 3) through fuse 63 (FIG. 3) and is returned through neutral wire 154. Grounding for the housing and pump is provided by ground wire 156 (FIG. 1).

Normally open mechanical safety switches and 108 on the front and rear panels 20 and 22, respectively, are electrically connected in series. In the embodiment represented in the drawings, the safety switches must be closed before power can be supplied through the fuse to the illuminated power switch 58 for operation of the unit. When the front and rear panels are secured in place on the housing, then the safety switches are closed and power is supplied to the power switch 58. However, when the power switch is activated, then no current is transmitted to the pump, fan, ozone generator, or reset switch unless the normally open contacts of safety relay 82 are closed.

Magnetic safety switch 54 on the lid for the sterilizing pan (FIGS. 3 and 7B) electrically connects relay switch 82 (FIGS. 3, 7A, and 7B) to the circuit for the unit in series between illuminated power switch 58 and reset switch 59 (FIG. 1). Relay switch 82 is bolted to the terminal strip with normally open contacts. Relay switch 82 includes a coil (FIG. 7B) that, when energized with current, creates a magnetic field to close the normally open safety relay contacts. The coil is energized and the safety relay switch is closed to complete the electrical circuit when the magnetic safety switch 54 is in place and power is supplied to the unit through the illuminated power switch. Coil 158 has an impedance sufficient to generate a current of about 10 amps, which is sufficient to operate the pump and transformer when the reset switch 59 is activated.

As shown in FIG. 7A, fan 92 and safety relay 82 are connected in parallel so that the fan can be operated whether or not the lid is in place. Power to the fan is supplied by terminal pairs 86 on terminal strip 78 (FIG. 3). Reset switch 59 on the switch plate activates a timer relay 80 for the sterilization cycle after the instruments are placed in the sterilization pan and power is supplied to the unit through power switch 58. Timer relay 80 is mounted on terminal strip 78 (FIG. 3).

Reset switch 59 preferably is an illuminated push button switch. Neutral wire 160 is provided for operation of the light and its timer relay. Reset switch 59 electrically is connected in series to the timer relay 80 and is illuminated for a predetermined time after the sterilization cycle has commenced to show that the unit has run for a period of time sufficient for sterilization. The timer relay activates a series connected circuit relay 84 (FIGS. 7A and 7C) for operation of the pump and transformer, which supplies power at high voltage to the ozone generator. Circuit relay 84 is mounted to the terminal strip 78 (FIG. 3) and includes a timer relay 162 and coil 164 (FIG. 7C) for generating current sufficient to operate the pump and to supply power to the primary coil of the transformer. The pump and transformer are electrically connected in parallel to the circuit relay.

The invention claimed herein has been described with respect to a specific embodiment illustrated in the drawings. However, the foregoing description is not intended to limit the invention to the illustrated embodiment, and the skilled artisan should recognize that variations can be made within the spirit and scope of the invention as described in the foregoing specification. On the contrary, the invention includes all alternatives, modifications, and equivalents that may be included within the spirit and scope of the invention as defined by the appended claims.

What is claimed is:

1. Apparatus for sterilizing articles comprising:

(a) an open chamber for containing articles to be sterilized, said chamber receiving a reciruclated supply of water containing ozone for immersion contact with the articles to be sterilized;

(b) an openable lid associated with said open chamber for substantially precluding ozone that escapes from the water from escaping from said chamber when said apparatus is being operated, said lid comprising an ozone destroying substance;

(c) means for recirculating a flow of the water containing ozone through said chamber sufficient for immersion contact of said articles in the ozone containing water, said recirculating means including:

i) an ozone generator of generating ozone, ii) a high voltage transformer for supplying power to said generator, said transformer being a step up transformer and having an output voltage of from at least about 8,000 to 12,000 volts;

iii) means for injecting ozone generated by said generator into water in a concentration of at least about 0.2 ppm;

iv) a pump having a fluid intake and a fluid discharge for recirculating water containing ozone at a pressure of from about 25 to 40 psig and at a rate of from about 1 to 4 gallons per minute;

iv) a first fluid flow conduit interconnecting said chamber and said intake side of said pump for flow from said chamber to said pump;

vi) a second fluid flow conduit interconnecting said ozone injecting means with said discharge side of said pump; and vii) a third fluid flow conduit interconnecting said ozone injecting means with said chamber for reciruclating flow of the water containing ozone through said chamber; and (d) safety means electrically connected to said lid for precluding the operation of said recirculating means when said lid is open.

2. The apparatus of claim 1 wherein said lid for closing said chamber comprises a perforated outer shell and said ozone destroying substance is located within said outer shell, whereby the ozone is destroyed upon contact with said substance, and said safety means comprises a magnetic safety switch located on said lid.

3. The apparatus of claim 1 wherein said means for injecting ozone into the water is a venturi and said apparatus further comprises a fourth fluid flow conduit interconnecting said ozone generator and said venturi, said venturi receiving ozone gas from said ozone generator and injecting the ozone into the water for supply of water containing ozone to said sterilizing chamber.

4. The apparatus of claim 3 wherein said recirculating means further comprises a check valve positioned between said venturi and said ozone generator substantially to preclude water from entering said generator.

5. The apparatus of claim 3 wherein said recirculating means further comprises an air drier and a fifth fluid flow conduit interconnecting said air drier and said ozone generator so as to supply dry air to said ozone generator.

6. The apparatus of claim 5 wherein said fifth fluid flow conduit extends from said ozone generator to said venturi for conducting ozone gas from said generator to said venturi, and wherein the vacuum created by said venturi draws air through said air drier and ozone generator in the absence of a compressor.

7. The apparatus of claim 1 wherein said ozone generator comprises at least one mercury-free corona tube spaced from a jacket electrode.

8. The apparatus of claim 1 wherein said recirculating means further comprises means for distributing the ozone-containing water evenly within said chamber and an aperture positioned in said chamber for gravity discharge of the water from said chamber.

9. The apparatus of claim 8 wherein said distributing means comprises an elongate, hollow distribution member positioned within said chamber for distributing the water containing ozone evenly throughout said chamber, said distribution member having a plurality of radially directed apertures along its length for distributing the water containing ozone into the interior of said chamber.

10. The apparatus of claim 1 further comprising a housing, and wherein said chamber is mounted in said housing and said recirculating means is located within said housing.

11. The apparatus of claim 10 wherein said chamber is integral with said housing, said chamber having four sides and a bottom and being open at the top, and said lid for closing said chamber is located at said top of said chamber, said lid comprising a substance for destroying ozone that escapes from the water containing ozone in said chamber.

12. The apparatus of claim 10 further comprising means for dissipating heat generated by operation of said apparatus from said housing.

13. The apparatus of claim 12 wherein said heat dissipating means includes vents in said housing and a fan positioned on said housing to exhaust air from said housing.

14. The apparatus of claim 13 wherein said fan is constructed and arranged to move at least about 100 cfm of heated air.

15. The apparatus of claim 10 wherein said recirculating means includes an on/off switch located on said housing and electrically connected to said ozone generator, a timer electrically connected to said ozone generator for controlling cycle time, and an indicator light on said housing and electrically connected to said timer for indicating when the apparatus has operated for a predetermined sterilizing period.

16. Apparatus of claim 10 further comprising a valve located on said housing for draining water from said chamber to the exterior of said housing.

17. Apparatus of claim 10 wherein said housing and said chamber are stainless steel and said housing includes a pair of handles to facilitate transporting said apparatus from one location to another.

18. Apparatus of claim 10 wherein said housing comprises panels of stainless steel sheet metal mounted so as to form a housing and wherein primary access to said recirculating means is through at least one of said panels, said housing further comprising one or more safety switches electrically connected to said housing for precluding providing electrical current to said recirculating means unless said access panels are mounted in place.

19. Apparatus of claim 10 further comprising panels of an inert and nonconductive insulating material located within said housing for insulating the housing from electrical discharge and to which said recirculating means is mounted.

20. Apparatus for sterilizing medical instruments comprising:

(a) a housing;

(b) an instrument sterilizing pan for containing instruments to be sterilized, said pan being integral with said housing and having an open top for receipt and removal of medical instruments, said pan being positioned for receiving a recirculated flow of water containing ozone sufficient for immersion contact of the medical instruments and sufficient to sterilize the medical instruments, said pan having an aperture positioned for gravity discharge of the water containing ozone;

(c) an openable lid cooperating with said open top of said instrument sterilizing pan, said lid comprising a perforated outer shell and an ozone destroying substance located within said outer shell, whereby ozone that escapes from the water is destroyed upon contact with said ozone destroying substance;

(d) means for recirculating flow of the water containing ozone through said instrument sterilizing pan at a pressure of from at least about 25 to 40 psig and at a rate of from at least about 1 to 4 gallons per minute, said recirculating means including an ozone generator located within said housing for generating ozone and a means for injecting ozone generated by said generator into the water in a concentration of at least about 0.2 ppm, a pump having a fluid intake and a fluid discharge, a first fluid flow conduit interconnecting said instrument sterilizing pan and said intake side of said pump for flow from said pan to said pump, a second fluid flow conduit interconnecting said ozone injecting means with said discharge side of said pump, and a third fluid flow conduit interconnecting said ozone injecting means with said pan for recirculating flow of the water containing ozone through said pan; and (e) a magnetic safety switch electrically connected to said lid for preventing operation of said recirculating means when said lid is open.

21. Apparatus for sterilizing medical instruments comprising:

(a) a housing;

(b) an instrument sterilizing pan for containing instruments to be sterilized, said pan being integral with said housing and having an open top for receipt and removal of medical instruments, said pan being positioned for receiving a recirculated flow of water containing ozone sufficient for immersion contact of the medical instruments and sufficient to sterilize the medical instruments, said pan having an aperture positioned for gravity discharge of the water containing ozone;

(c) an openable lid for said instrument sterilizing pan, said lid comprising a perforated outer shell and an ozone destroying substance located within said outer shell, whereby ozone that escapes from the water is destroyed upon contact with said ozone destroying substance;

(d) means for recirculating flow of the water containing ozone through said instrument sterilizing pan at a pressure of from at least about 25 to 40 psig and at a rate of from at least about 1 to 4 gallons per minute, said recirculating means including an ozone generator located within said housing for generating ozone, said ozone generator comprising at least one mercury-free corona tube spaced from a stainless steel jacket, said recirculating means also including a venturi positioned for injecting ozone from said ozone generator into the water containing ozone in a concentration of from about 0.2 to 0.6 ppm, a pump having a fluid intake and a fluid discharge, a first fluid flow conduit interconnecting said instrument sterilizing pan and said intake side of said pump for flow from said pan to said pump, a second fluid flow conduit interconnecting said venturi with said discharge side of said pump, a third fluid flow conduit interconnecting said venturi with said pan for recirculating flow of the water containing ozone through said pan, and a fourth fluid flow conduit interconnecting said venturi and said ozone generator, said venturi receiving ozone gas from said ozone generator and injecting ozone into the water for supply of water containing ozone to said pan; and (e) a magnetic safety switch electrically connected to said lid for preventing operation of said recirculating means when said lid is removed.

\* \* \* \* \*

UNITED STATES PATENT AND TRADEMARK OFFICE
CERTIFICATE OF CORRECTION

PATENT NO. : 5,520,893
DATED : May 28, 1996
INVENTOR(S) : Kasting, Jr. et al

It is certified that error appears in the above-indentified patent and that said Letters Patent is hereby corrected as shown below:

Column 8, line 43, after "switches" insert -- 106 --.

Column 8, line 60, after "coil" insert -- 158 --.

Column 9, line 53, "of" should be -- for --.

Column 9, line 65, "iv)" should be -- v) --.

Signed and Sealed this

Seventeenth Day of September, 1996

Attest:

BRUCE LEHMAN

Attesting Officer    Commissioner of Patents and Trademarks